United States Patent [19]
Joslyn

[11] Patent Number: 4,759,909
[45] Date of Patent: Jul. 26, 1988

[54] METHODS AND APPARATUS FOR STEAM STERILIZATION

[75] Inventor: Larry Joslyn, Macedon, N.Y.

[73] Assignee: Joslyn Valve Corp., Macedon, N.Y.

[21] Appl. No.: 919,948

[22] Filed: Oct. 17, 1986

Related U.S. Application Data

[63] Continuation-in-part of Ser. No. 417,189, Feb. 23, 1983, abandoned.

[51] Int. Cl.⁴ ............................ A61L 2/06; A61L 2/08
[52] U.S. Cl. ............................................ 422/26; 422/3; 422/110; 422/116; 422/295
[58] Field of Search .................. 422/26, 28, 107, 110, 422/3, 295, 116

[56] References Cited

U.S. PATENT DOCUMENTS

| | | | |
|---|---|---|---|
| 3,088,180 | 5/1963 | Lauterbach | 422/26 X |
| 3,444,725 | 2/1969 | Irons et al. | 422/26 |
| 3,481,692 | 12/1969 | Linder | 422/26 X |
| 3,944,387 | 3/1976 | Schreckendgust | 422/3 |
| 3,967,494 | 7/1976 | Joslyn | 422/26 X |
| 4,115,068 | 9/1978 | Joslyn | 422/56 |
| 4,164,538 | 8/1979 | Young et al. | 422/26 |
| 4,294,804 | 10/1981 | Baran | 422/28 X |
| 4,309,385 | 1/1982 | Chamberlain et al. | 422/3 |
| 4,324,761 | 4/1982 | Mastrup et al. | 422/163 X |
| 4,457,892 | 7/1984 | Young | 422/3 X |

OTHER PUBLICATIONS

Block, *Disinfection, Sterilization and Preservation* (1977), pp. 493–508.
Halleck, "Symposium: Industrial Sterilization and Regulatory Aspects", 18, Aug. (1976), pp. 335–351.
Perkins et al., *Principles and Methods of Sterilization in Health Sciences*, (1969), 2nd Ed., pp. 110–114, 150–152, 501–530.

*Primary Examiner*—Barry S. Richman
*Assistant Examiner*—Jill Johnston
*Attorney, Agent, or Firm*—Martin LuKacher

[57] ABSTRACT

Methods and apparatus for steam sterilization in which goods are conditioned by removing air and heated to a desired temperature in a chamber. The goods are subjected to a plurality of pressure pulses at above atmospheric pressure by alternate pressurization and venting of the chamber to atmospheric pressure. At the beginning of the process and following pressurization pulses, at or slightly above atmospheric pressure air is flushed from the chamber with steam prior to pressurization. Upon removal of air from the load and the chamber sterilizing environment, the chamber is pressurized until a selected pressure related sterilization temperature is reached. After a timed exposure period, the sterilizing chamber is vented to atmospheric pressure and a vacuum is created in the sterilizing chamber to dry the load.

10 Claims, 2 Drawing Sheets

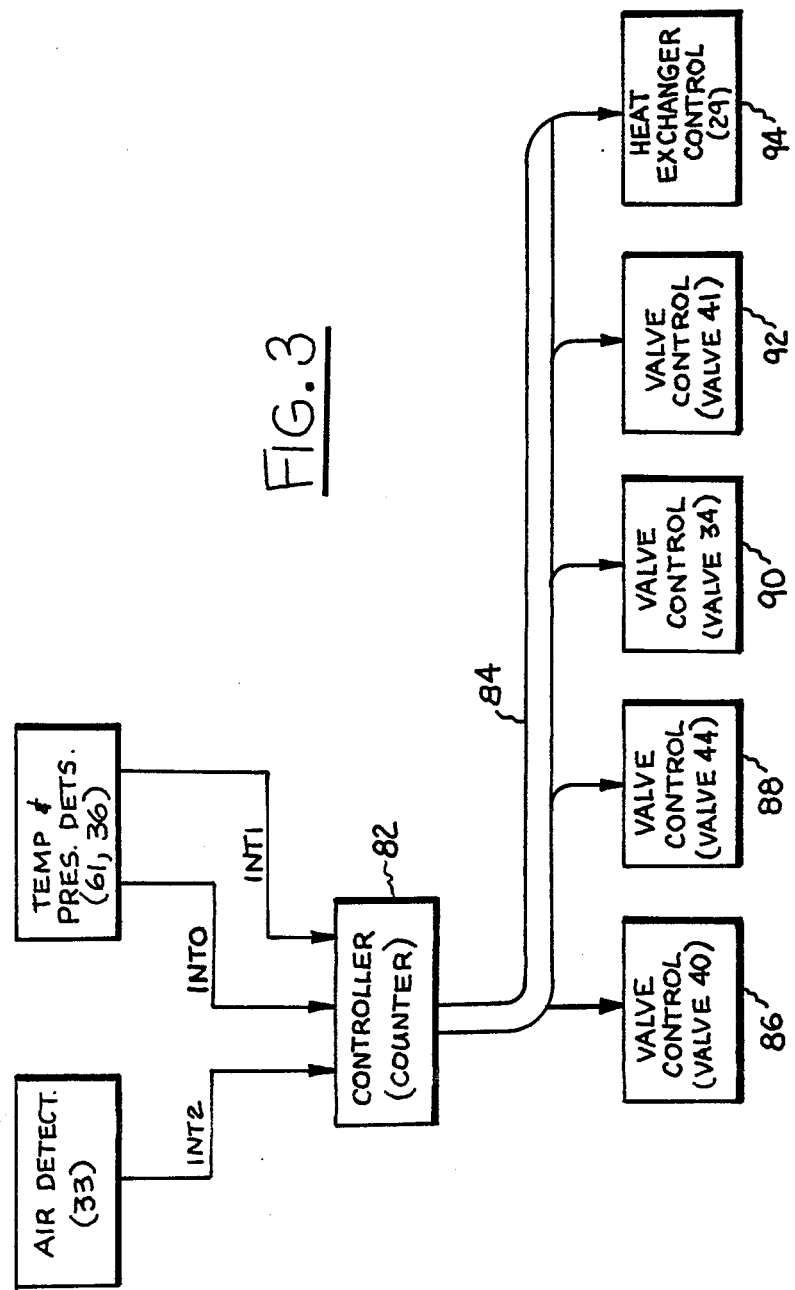

METHODS AND APPARATUS FOR STEAM STERILIZATION

DESCRIPTION

This application is a continuation-in-part of application Ser. No. 417,189 filed Feb. 23, 1983, now abandoned.

This invention relates to steam sterilization, and particularly to methods and apparatus for steam sterilization with removal of air from the sterilizing environment and the load to provide uniform, rapid heating of goods to be sterilized. The invention is especially suitable for use with automated sterilizer control devices and methods for reliable removal and measurement of air removed from the load and sterilizing environment at optimum efficiency of time and energy.

Chamber air is the most detrimental factor to efficient steam sterilization. Air prevents steam from penetrating all portions of a load. Temperature variation in a steam environment and cold spots occurring in a load during sterilization are generally related to air in the sterilizing chamber. Since this detracts from sterilizing efficiency, proper conditioning of loads, which includes fabrics, requires substantially complete removal of air from the interstices of the load and the sterilizing chamber.

Various methods for removing air from sterilizing chamber and load have been taught (J. J. Perkins, Principles and Methods of Sterilization in Health Sciences, Publisher—C. C. Thomas, Springville, Ill., Pages 150–152; J. J. Perkins, Disinfection, Sterilization & Preservation, Publisher—Lee & Febiger, Phila., Pa., Pages 505–507; U.S. Pat. No. 3,409,389; and U.S. Pat. No. 3,494,725), including high vacuum, steam pulsing above atmospheric pressure, steam pulsing below atmospheric pressure and a combination of pulsing above and below atmospheric pressure. Past pressure pulsing methods above atmospheric pressure to remove air require more time than pressure pulsing below atmospheric pressure, but are not affected by sterilizing chamber leaks. High vacuums, and pressure pulsing below atmospheric pressure generally require less conditioning time to remove air but unreliability of mechanical systems can result in ineffective load heating if chamber air leaks occur.

It has been discovered, in accordance with the invention that the optimum sterilization process is to provide for removal of air from the chamber and load at above atmospheric pressure with a short conditioning period.

The present invention provides an improved method and apparatus for sterilization by efficient automated and accurate load conditioning and load heating at above atmospheric pressure. Sterilization apparatus in accordance with the invention uses strategic location and design of the sterilizing chamber steam entry inlet area and the vent discharge to produce efficient gravity displacement of air from the sterilizing chamber. In accordance with the invention gravity displacement of air from the sterilizing chamber at substantially atmospheric pressure is used alternately and in conjunction with a controlled pulsing action. This combination of gravity displacement and pulsing action provides drive power for removing air from a load and the sterilizing environment. The efficiency of this method reduces cycle time to substantially that which can be achieved with various preconditioning methods performed below atmospheric pressure. The advantages of rapid heating and short conditioning times at above atmospheric pressure are achieved while adding accuracy of conditioning and dependability of operation even where the sterilizing chamber may have mechanical problems producing air leaks.

Another feature of the present invention is to provide automated and accurate conditioning control which monitors the load and the sterilizing chamber with load sensors in contact with the load and without requiring prejudgment of the load by the operator. In accordance with this feature of the invention, the chamber and load characteristics are measured as a function of the measurement of air discharged from the sterilizing chamber during gravity displacement. Such measurements provide indication of dependable and complete conditioning while enabling conservation of both time and energy.

Still another feature of the present invention is to provide rapid drying of the load following sterilization without requiring mechanical apparatus to pump the moisture from the sterilizing chamber. In accordance with this feature of the present invention moisture is removed from the load and sterilizing environment by condensing chamber steam directly by means of a heat exchanger. As steam rapidly collapses in the heat exchangers, a vacuum is created in the sterilizing chamber which draws moisture from within the load.

The present invention is applicable to and may be used with or embodied in any of the standard sizes of sterilizers used commercially. When so used or embodied the invention provides for complete conditioning, load heating and drying to facilitate desired sterilization in the shortest practical time and to provide dry loads in order to maximize sterility maintenance of products which have been sterilized.

Other advantages and contributions of the invention will be more apparent from a reading of the following description, detailing methods and presently preferred apparatus in accordance therewith which are shown in the accompanying drawings, in which:

FIG. 3 is a block diagram showing the control circuits of the apparatus of FIG. 1 in greater detail.

Figure 1:
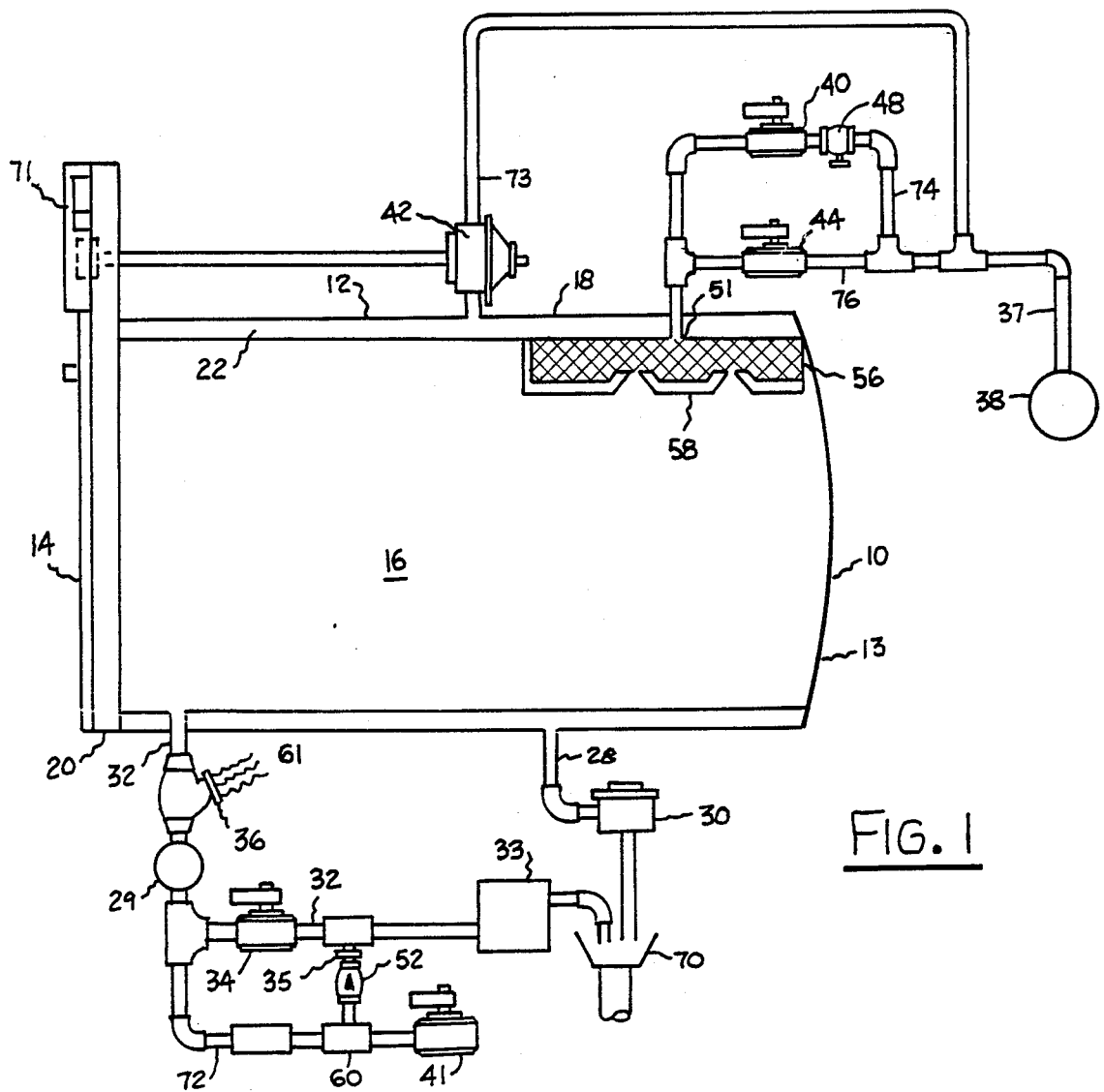
FIG. 1 is a schematic diagram of sterilizing apparatus embodying the invention.

In FIG. 1, there is shown a sterilizer 10 having a double-walled chamber 16. The chamber 16 has an inner open-ended wall vessel 12 with an end closure 13, and a door 14. The chamber 16 has an outer wall 18 which is spaced outwardly therefrom and circumscribes a major portion of the wall 12. An open end of the outer wall 18 is joined to the adjacent end of the inner wall 12 by a flange 20 to define a steam jacket 22 between the inner and outer walls. The door 14 can be hinged or otherwise mounted to facilitate opening and closing of the chamber 16. A conventional lock assembly can be used for the door 14, e.g. a cam lock assembly or a sliding channel flange 20 enabling the door to be firmly locked to seal the chamber 16 during the sterilizing operation.

The jacket 22 and chamber 16 are separately controlled for discharge purposes. A drain line or conduit 28 connects the jacket 22 to a thermostatic steam trap 30 which discharges condensate from the jacket 22 into a conventional sewer drain 70.

A second drain conduit 32 is connected between vessel 12 and conventional heat exchanger 29. A valve 34, connected in the drain conduit 32, controls the flow of steam, condensate or other fluid from the chamber 16 through a heat exchanger 29 into a conventional air detection device generally indicated at 33 (see U.S. Pat. No. 3,967,494 for a suitable air detection device). Excess condensate overflows from the air detection device 33 into the waste sewer drain 70. A temperature sensing bulb 36 and a pressure sensor 61 are mounted up-stream of the heat exchanger 29 and adjacent to the outer chamber wall 18 to measure the temperature and pressure of steam flowing from the sterilizing chamber 16 for control of the steam supply during preconditioning and sterilizing. A check valve 52, a bleed orifice 35, and an air filter 60, are connected to branch 72 of drain conduit 32 to remove chamber air and condensate, when the chamber 16 is pressurized. The two branches 32 and 72 of the drain conduit 32 are joined between the bleed orifice 35 and control valve 34 to discharge into the air detection device 33. A vent control valve 41 for air is connected in the branch 72 of the drain pipe 32.

The heat exchanger 29 is used to condense steam from the sterilizing chamber during gravity displacement, venting, and on drying. The heat exchanger 29 reduces the volume of steam which passes through the drain conduit 32 to discharge such that the size of control valve 34 and drain conduit 32' can be reduced, while maintaining a high mass discharge flow rate. Other advantages of the heat exchanger 29 will be more apparent from the presentation of the methods and description of the apparatus operation, which follows hereinafter. The valve 34 and the other control valves mentioned hereafter have power measure for their operation automatically. Handles on these valves are shown in the drawing to illustrate that they also may be manually opened and closed.

A main steam supply line or conduit 37 connects a source of steam, such as a boiler 38, to the steam jacket 22 and the sterilizing chamber 16 through a plurality of branches 73, 74 and 76 of conduit 37. A pressure regulator 42 is connected in one branch 73 of the steam supply conduit 37 to control the flow of steam into the jacket 22. Pressure regulator 42 cooperates with steam trap 30 to maintain steam pressure, and consequently constant temperature in the jacket 22.

Steam is supplied to the sterilizing chamber 16 through two branches 74 and 76 of the steam supply conduit 37. A control valve 44 connected to one branch 76 supplies steam to the sterilizing chamber 16 at a very high rate. A control valve 40 and a metering valve 48 connected in another branch 74 supplies steam to the sterilizing chamber 16 at a reduced rate. Both branches feed steam into the chamber 16 through a water separator 56 and a baffle 58 which covers the steam inlet 51. Completing the basic structure for the illustrated sterilizer of the present invention is a control panel 71 comprised of conventional timing, electrical contact closure, pressure and temperature signal measuring and programmable control logic devices (also, see FIG. 3). The panel 71 is used to receive and issue signals to sequence the sterilization process control function.

Figure 2:
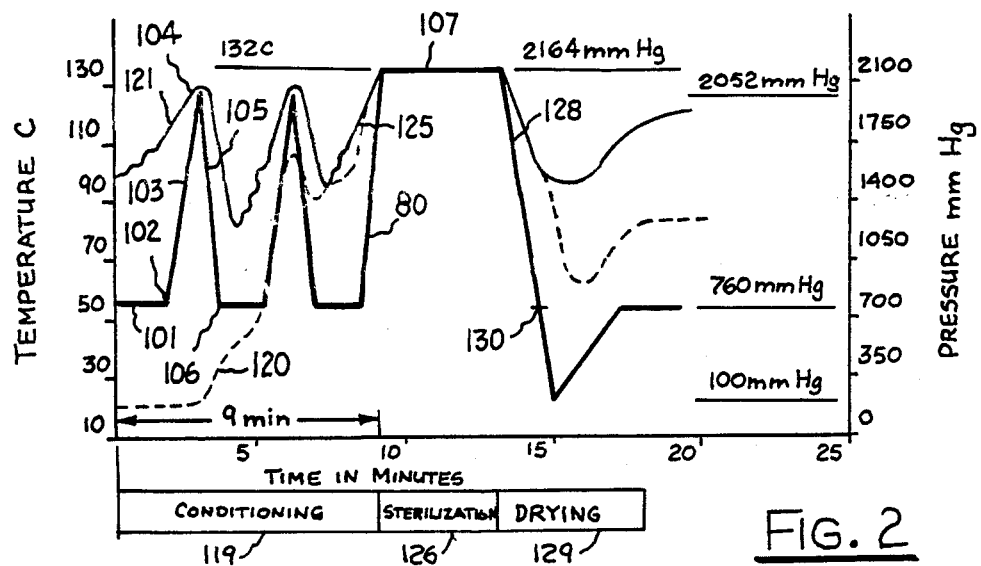
FIG. 2 is a graphic representation of a method of practicing the invention showing conditioning, sterilization and drying of a typical fabric load.

Referring to FIG. 2, there is shown the operation of the sterilization apparatus to remove air by the alternate use of gravity displacement and pressure pulses for a load and chamber conditioning 119 phase followed by a sterilization phase 126 at a temperature related exposure period and a drying phase 129 for a drying of the load.

FIG. 2 also is the graphic representation of the method of practicing the invention. The sterilizer 10, is prepared for operation by adjusting the jacket 22 pressure regulator 42 to a pressure related temperature typically 3°–5° C. higher than the temperature at which the sterilization process will be performed.

Upon initiating a sterilization cycle, steam is admitted to the top of the sterilizing chamber 16 from the boiler 38 through conduit 37, metering valve 48, control valve 40, water separator 56 and baffle 58. Simultaneously, and at substantially the same rate, the chamber is vented through conduit 32, temperature sensor 36, heat exchanger 29, and control valve 34 to the air detection device 33. The heavy line curve 80 in FIG. 2 shows a graphic profile of the variation of the temperature related pressure in the chamber 16 with time. This pressure initially during the conditioning phase is substantially at atmospheric pressure as shown at 101 in FIG. 2. Because steam is light relative to air, the steam forms a stratified layer across the top of the sterilizer 10. Although air is diffusing into the steam layer, as a related rates function, the steam mass displaces the air downward faster than the air can diffuse into the constantly renewed supply of pure steam; the steam waive front acting as a piston driving air in the chamber 16 out of the chamber 16 through the bottom conduit 32. Metering valve 48 is adjusted to maximize the air displacement efficiency relative to the amount of steam consumed.

The water separator 56 and the steam baffle 58 play important roles in the gravity displacement. High velocity steam, even flowing through well trapped steam supply piping, carries a considerable amount of entrained water. This results in poor steam quality, which on contact produces wet loads. The water separator 56 consists of materials which introduce tortuous paths for steam molecules to pass through. Steam molecules readily pass through the maze while heavier atomized water particles and entrained water collide with the separator path walls in the separator 56 where they coalesce and drain out of the bottom portion of the separator 56. The baffle 58 directs steam to the chamber 16 top and water to the chamber drain conduit 32. Water separators made from porous stones, metals and plastic have demonstrated acceptable characteristics in this application.

The steam separator 56, in conjunction with the baffle 58, also performs the function of reducing the velocity of steam entering the chamber 16. If the steam enters the chamber 16 at a high velocity, flow turbulence causes the steam to mix with air rather than to form a stratified steam layer across the top of the sterilizer. Although this air can be flushed from the chamber 16 by mass flow dilution in which case the baffle 58 and branch 74 may not be needed and the steam may be directly admitted into the chamber 16, this is less efficient. Experimentally, it has been found that reducing the steam velocity entering the chamber 16 to substantially 1 ft/sec or less minimizes the amount of steam and air mixing.

After a predetermined time interval, typically 1.5 to 2 minutes, or when the vent drain line 32 discharge air drops below a given concentration as measured with the air detection device 33, the first gravity displacement step of the conditioning phase 119 is terminated and a pressure pulse is initiated as shown at 102 of FIG. 2. Vent conduit 32 control valve 34 is closed, the heat exchanger 29 is shut off and the chamber steam supply valve 44 is opened. This causes the chamber 16 pressure to rise rapidly as shown generally at 103 in FIG. 2. The pressure rise is generally terminated at a temperature related limit which will not exceed a temperature which the load being sterilized can withstand. As the chamber 16 is pressurized with steam, load air is compressed within the load by the steam in the chamber 16, from substantially atmospheric pressure to peak partial pressure equivalent to the peak of the pressure pulse shown at 104 in FIG. 2. The steam rapidly heats the portions of the load from which the air has been displaced by compression through heat of condensation.

Upon attaining the temperature related peak pressure 104, which is indicated and may be initiated by control of signals from the control panel 71, the sterilizing chamber is vented to substantially atmospheric pressure as shown generally at 105 in FIG. 2. This is achieved by closing steam supply valves 40 and 44 while activating the heat exchanger 29 and opening vent control valve 34. On venting the chamber 16, the air in the load expands corresponding with the decrease in chamber 16 steam pressure. A portion of the steam which condensed in the load during pressurization picks up load heat and revaporizes as the chamber 16 pressure decreases. This provides a driving force to push air from the load into the chamber 16 environment. Experience has shown that only the amplitude of the pressure pulse (102 to 104 to 106) and not the time for a pulse is of major importance in removing air from the load; thus the time for pressurization 103 and venting 105 can be minimal.

After reaching substantially atmospheric pressure as shown at 106, the gravity displacement and pressure pulse procedure is repeated until air is sufficiently removed from the system such that the load temperature, shown generally at 120 by the dotted line curve, converges with chamber temperature 125, as shown by the thin line curve 121 in FIG. 2. It has been found that this heating characteristic occurs when little or no chamber 16 air is measured by the air detection device 33 when the sterilizing chamber 16 is vented to atmospheric pressure and followed by gravity displacement. It has also been found that for a given pressure pulse amplitude and gravity displacement time interval, removal of air can be repeatedly achieved within a fixed number of pressure pulses, each followed by gravity displacement. For pressure pulses with an amplitude between 15 to 27 psi followed by gravity displacement time intervals of 1.5 to 2 minutes, it has been demonstrated that adequate chamber and load conditioning to remove air can be achieved within 4 to 2 pulses respectively.

When the conditioning phase 119 of the cycle is completed, the sterilizing chamber 16 is pressurized to a temperature related pressure as shown at 107 in FIG. 2. Vent conduit control valve 34 is closed, the heat exchanger 29 is shut off and the steam supply valve 44 is opened. When the selected sterilizing temperature is attained in the sterilizing chamber, steam supply valve 44, in response to temperature sensor 36, turns on and off to maintain a selected sterilization temperature also as shown at 107 in FIG. 2. The chamber 16 temperature is maintained for a temperature related exposure time to sterilize the load in the sterilizing chamber 16. At the end of the exposure time, the sterilization phase 126 of the cycle is complete, and the drying phase 129 of the cycle is initiated.

During the drying phase 129, the steam supply valve 44 is closed, the vent conduit control valve 34 is opened and the heat exchanger 29 is turned on. This results in a decrease in chamber pressure as shown at 128. When the chamber pressure approaches atmospheric pressure (shown at 130 in FIG. 2), drain vent valve 34 is closed. Steam remaining in the chamber 16, upon coming in contact with the heat exchanger 29, condenses and creates a vacuum in the sterilizing chamber 16. The ultimate vacuum level attained will be substantially equivalent to the partial pressure of steam at the heat exchanger 29 temperature. The chamber vacuum allows moisture within the load to pick up load heat, revaporize and be drawn from the load. The very deep vacuum that is attainable by condensing chamber steam with the heat exchanger 29 results in loads which are substantially dry. After reaching a predetermined vacuum level, typically 50 to 100 mm Hg absolute, or after a timed interval, air is admitted to the chamber through the bioretentive filter 60 by opening the air vent control valve 41. When the chamber 16 reaches atmospheric pressure the cycle is complete and the load may be removed for use.

The cycle shown in FIG. 2 may be implemented by techniques know in the art, as shown in FIG. 3, which uses a process controller 82 containing a counter for keeping track of sequencing. Such a process controller may be a microprocessor chip which receives interrupts from the pressure and temperature detectors 61 and 36 (INT0 and INT1) and form the air detector 33 (INT2). The power means of the valves, e.g. control solenoids, provides valve controls 86, 88, 90, and 92, and there is a similar control 94 for the heat exchanger 29. The controller produces a sequence of commands over the bus 84 to the controls 86 to 92 to affect the operations shown in FIG. 2 and described above.

While specific embodiments of the invention have been disclosed and described, it is to be understood that the invention is not intended to be restricted to such embodiments but, rather, all embodiments which in view of the present teaching, come within the spirit and scope of the invention.

I claim:

1. A method of conditioning, steam sterilizing, and drying materials comprising the steps of:
   (1) loading said materials into a sealable chamber capable of operation at other than atmospheric pressure and sealing the chamber;
   (2) conditioning the loaded materials which comprises the steps of
      (a) removing air from the chamber by gravity displacement with steam at atmospheric pressure, initiating a plurality of alternating above atmospheric pressure pulses and at least atmospheric pressure gravity displacement phases, wherein the pressure pulses are below an upper pressure related to a desired steam sterilization temperature achieved by injecting steam into the chamber, and wherein each of the alternating pressure pulses includes venting the chamber to atmospheric pressure, and wherein each of the alternating pressure pulses is followed by a gravity displacement phase during which air is displaced from the chamber by steam at substantially atmospheric pressure,
      (b) measuring the air being discharged from the chamber by an air detection means during each gravity displacement phase thereby providing an indication of residual air in the load and the chamber, (c) timing the duration of each gravity displacement phase, (d) continuing alternating pulses pressure gravity displacement phases until air is sufficiently removed from the chamber; and (e) controlling the termination of conditioning of the loaded materials and the initiation of heating the loaded materials to the desired sterilization temperature automatically in response to the measurement of air being discharged from the chamber during the gravity displacement phases;

(3) sterilizing the loaded materials which comprises the steps of introducing and maintaining sterilizing steam in the chamber at a pressure level to maintain the desired temperature for a time sufficient to affect desired sterilization of the materials; and (4) drying the loaded materials which comprises the steps of (a) venting the chamber to atmospheric pressure by discharging steam in the chamber to a drain while the pressure in the chamber is maintained above atomospheric pressure, (b) producing a vacuum in the chamber by condensing steam in the chamber, and (c) introducing air into the chamber to atmospheric pressure through a bacterial retentive filter to maintain sterile conditions in the chamber.

2. The method of claim 1 wherein the step of removing air from the chamber by gravity displacement further comprises purging air from the chamber by injecting steam into the chamber while simultaneously venting steam and air from the chamber.

3. The method of claim 1 wherein said venting of said steam to said drain comprises
(a) condensing said steam with a heat exchanger means, and
(b) discharging the condensate to said drain.

4. The method of claim 1 in which gravity displacement of air from the sterilizing chamber is at slightly above atmospheric pressure.

5. The method of claim 1 in which the step of controlling the termination of load conditioning comprises
(a) continuing the alternating pulses pressure gravity displacement phases until a predetermined quantity of air is discharged from the chamber, and then
(b) terminating the loaded materials conditioning phase and initiating the pressurization of the chamber with steam until the chamber is substantially equal to a predetermined upper pressure related to the desired sterilization temperature.

6. The method of claim 1 wherein the initial gravity displacement time is 1.5 to 2 minutes.

7. The method of claim 1 wherein the conditioning of the loaded materials further includes selecting the number of pressure pulse-gravity displacement phases relative to a predetermined pressure pulse differential pressure and an air purge gravity displacement time.

8. A steam sterilizing method including a conditioning phase for removing air from a sterilizing chamber comprising:

(a) a conditioning phase which comprises
(1) introducing steam into said chamber for a timed period while maintaining said chamber at substantially atmospheric pressure in order to displace air from said chamber,
(2) pressurizing said chamber with steam to a peak above atmospheric pressure not greater than the pressure corresponding to the temperature of saturated steam at the desired sterilizing temperature,
(3) terminating said pressurizing step (2) by venting said chamber to substantially atmospheric pressure upon reaching said peak pressure within said chamber, and
(4) repeating steps (1) to (3) in sequence for at least one additional cycle; and (b) a sterilizing phase which comprises pressurizing said chamber with sterilizing steam to a pressure level related to the desired sterilizing temperature and maintaining said pressure for a time sufficient to effect sterilization.

9. A steam sterilizing method including a conditioning phase for removing air from a sterilizing chamber comprising:

(a) a conditioning phase which comprises
(1) introducing steam into said chamber for a timed period while maintaining said chamber at substantially atmospheric pressure in order to gravity displace air from said chamber,
(2) pressurizing said chamber with steam to a peak above atmospheric pressure not greater than the pressure corresponding to the temperature of saturated steam at the desired sterilizing temperature
(3) terminating said pressurizing step (2) and venting said chamber to substantially atmospheric pressure upon reaching said peak pressure within said chamber,
(4) repeating steps (1) to (3) in sequence for at least one additional cycle; and (b) a sterilizing phase which comprises pressurizing said chamber with sterilizing steam to a above atmospheric pressure level related to the desired sterilizing temperature and maintaining said pressure for a time sufficient to effect sterilization.

10. A method of removing air from a sealable steam sterilizing chamber capable of operating at other than atmospheric pressure and from materials loaded in the chamber which comprises (a) loading said materials into said chamber and sealing said chamber,
(b) removing air from the chamber by gravity displacement with steam substantially at or above atmospheric pressure, and
(c) initiating a plurality of cyclic above atmospheric pressure pulses and gravity displacement phases, each such pulse being followed by a gravity displacement phase during which air is displaced from the chamber by steam substantially at or above atmospheric pressure.

* * * * *